(12) United States Patent
Hibbs

(10) Patent No.: US 7,015,011 B2
(45) Date of Patent: Mar. 21, 2006

(54) CIRCUIT AND METHOD TO NON-INVASIVELY DETECT THE ELECTRICAL POTENTIAL OF A CELL OR NEURON

(75) Inventor: Andrew D. Hibbs, La Jolla, CA (US)

(73) Assignee: Electronic Biosciences, LLC, San Diego, CA (US)

( * ) Notice: Subject to any disclaimer, the term of this patent is extended or adjusted under 35 U.S.C. 154(b) by 200 days.

(21) Appl. No.: 10/418,993

(22) Filed: Apr. 18, 2003

(65) Prior Publication Data

US 2004/0207410 A1 Oct. 21, 2004

(51) Int. Cl.
*C12Q 1/02* (2006.01)
*C12M 1/34* (2006.01)

(52) U.S. Cl. ............... 435/29; 435/287.1; 204/403.01; 205/777.5

(58) Field of Classification Search ................. 435/29, 435/30, 32, 33, 287.1, 287.9, 288.3, 288.4; 436/63, 149; 422/82.01, 82.02; 324/61, 324/663; 204/403.01; 205/777.5
See application file for complete search history.

(56) References Cited

U.S. PATENT DOCUMENTS

| | | | |
|---|---|---|---|
| 3,903,874 A | 9/1975 | Shakespeare | |
| 3,967,628 A | 7/1976 | Vredenbregt | |
| 4,216,462 A | 8/1980 | McGrath et al. | |
| 4,641,664 A | 2/1987 | Botvidsson | |
| 4,649,924 A | 3/1987 | Taccardi | |
| 4,699,147 A | 10/1987 | Chilson et al. | |
| 4,777,955 A | 10/1988 | Brayton et al. | |
| 4,890,623 A | 1/1990 | Cook et al. | |
| 5,485,092 A | 1/1996 | Fortin | |
| 5,488,677 A | 1/1996 | Tokano | |
| 5,574,805 A | 11/1996 | Toba et al. | |
| 5,670,870 A | 9/1997 | Muramatsu | |
| 5,781,003 A | 7/1998 | Kondo | |
| 5,896,035 A | 4/1999 | Takahashi | |
| 6,051,422 A * | 4/2000 | Kovacs et al. | ........... 435/287.1 |
| 6,438,413 B1 | 8/2002 | Taheri | |
| 6,602,399 B1 | 8/2003 | Fromherz et al. | |
| 2003/0022387 A1 * | 1/2003 | Oka et al. | ................... 436/149 |

OTHER PUBLICATIONS

Weis et al., "Frequency Dependent Signal Transfer in Neuron Transistors", The American Physical Society, vol. 55, No. 1, pp. 877-889, Jan. 1997.

Weis et al., "Neuron Adhesion on a Silicon Chip Probed by an Array of Field-Effect Transistors", The American Physical Society, vol. 76, No. 2, pp. 327-330, Jan. 8, 1996.

Straub et al., "Recombinant Maxi-K Channels on Transistors, a Prototype of Iono-Electronic Interfacing", Nature Biotechnology, vol. 19, pp. 121-124, Feb. 2001.

Fromherz et al., "A Neuron-Silicon Junction: A Retzius Cell of the Leech on an Insulated-Gate Field-effect Transistor", Science, vol. 252, pp. 1290-1292, May, 1991.

* cited by examiner

*Primary Examiner*—William H. Beisner
(74) *Attorney, Agent, or Firm*—Diederiks & Whitelaw, PLC

(57) ABSTRACT

A system and method for non-invasively measuring the electrical potential radiated by a cell. To do this, a probe is positioned within ten microns distance from the cell for receiving the signal. Also, a reference potential is determined for the cell's environment. A sensor records the signal and compares the reference potential to the cell's signal to measure the electrical potential of the cell.

23 Claims, 2 Drawing Sheets

CIRCUIT AND METHOD TO NON-INVASIVELY DETECT THE ELECTRICAL POTENTIAL OF A CELL OR NEURON

FIELD OF THE INVENTION

The present invention pertains generally to systems and methods for measuring electrical fields. More specifically, the present invention pertains to systems and methods for measuring extremely small electrical fields produced by a living cell with the nutrient medium surrounding it. The present invention is particularly, but not exclusively, useful for systems and methods that can non-invasively measure the free-space electric field potential of cells, such as biological entities from the group including animal cells, plant cells, neurons, bacterial specimens and amoebae.

BACKGROUND OF THE INVENTION

Living cells, including neurons, exhibit electrical potentials that, although quite small, can be measured. For example, the total charge contained in a typical cell is approximately $5 \times 10^{-13}$ C, when measured for a voltage of −50 mV relative to the nutrient bath in which the cell is maintained. Obviously, obtaining such measurements can be difficult. Nevertheless, the effort may be worthwhile because a measurement of a cell's electrical potential contains information that can be very useful for evaluating the health and chemical composition of the cell. Such information may be particularly useful when successive measurements of a cell can be taken over extended periods of time. In addition, a cell's electrical potential may change in response to the exposure of the cell to a biological, chemical or pharmacological substance. Thus, the measurement of this change can be useful in detecting the presence of one of these substances.

Existing methods for measuring the electrical potential of a cell include procedures that require the insertion of a probe into the cell, or direct contact between the probe and the membrane of the cell. Fromherz et al., however, have proposed another approach for measuring the electrical potential of a cell which uses a custom-built field effect transistor (FET). This method relies on a capacitive coupling between the cell and the transistor that is on the order of picofarads. Consequently, the distance between the cell and the transistor must be around five one-hundredths of a micron (0.05 μm). As will be appreciated by the skilled artisan, this is a very small distance, and is virtually tantamount to actual contact.

In light of the above, it is an object of the present invention to provide a non-invasive system and method for measuring the electrical potential produced by a cell, in which the active electronics do not have to be in the immediate vicinity of the cell. Another object of the present invention is to provide a system and method for non-invasively measuring the electrical potential of the cell that is effective when the region of the probe that couples to the electric potential produced by the cell and passes the signal to the first stage electronics is as much as ten microns (10 μm) distant from the cell. Still another object of the present invention is to provide a system and method for measuring the electric potential produced by the cell within the nutrient bath that surrounds it, so that the cell can be maintained for extended periods of time in its required nutrient and electrolyte environment, without the cell being substantially disturbed. Yet another object of the present invention is to provide a system and method for measuring the electrical potential of a cell to determine whether the cell has been exposed to one or more biological, chemical or pharmacological substances. Another object of the present invention is to provide a system and method for measuring the electrical potential of a cell that is easy to use, is relatively simple to manufacture and is comparatively cost effective.

SUMMARY OF THE INVENTION

A system for non-invasively measuring the electrical potential of a cell includes, in combination, a reference electrode, a probe, a sensor and a comparison means, such as a computer, or an operational amplifier. In overview, the cell radiates an electromagnetic signal that is received by the probe and subsequently recorded by the sensor. The computer (operational amplifier) then compares this signal to a reference potential that is determined by the reference electrode, to measure the electrical potential of the cell. For the present invention all varieties of cells are contemplated, including such biological entities as: animal cells, plant cells, neurons, bacterial specimens and amoebae.

In use, the probe is immersed or is built into a nutrient bath wherein the cell to be evaluated is located. More specifically, the probe is positioned so that its detection surface is within a predetermined distance from the cell (e.g. within ten microns (10 μm) from the cell). This positioning allows the conducting surface of the probe to receive the signal that is radiated from the cell. Preferably, in order to optimize signal reception, the conducting surface of the probe, and the cell will have a substantially same spatial extent (i.e. they will be about the same size). After being received, the signal is electronically passed from the conducting surface to the sensor for recording.

Along with the probe, a reference electrode is also immersed or is built into the nutrient bath. As the probe receives the signal from the cell, the reference electrode is used to determine a reference potential for the bath. The potential of the cell is measured relative to this reference potential. As envisioned for the present invention, when the signal that is radiated by the cell has a frequency greater than about ten Hertz (>10 Hz), the sensor will be able to record the signal with a signal to noise ratio (SNR) greater than one (SNR>1). It is also envisioned for the system of the present invention that the sensor may record signals that are simultaneously radiated from a plurality of cells. In this case, the sensor will use the resultant plurality of signals to measure an integrated response.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
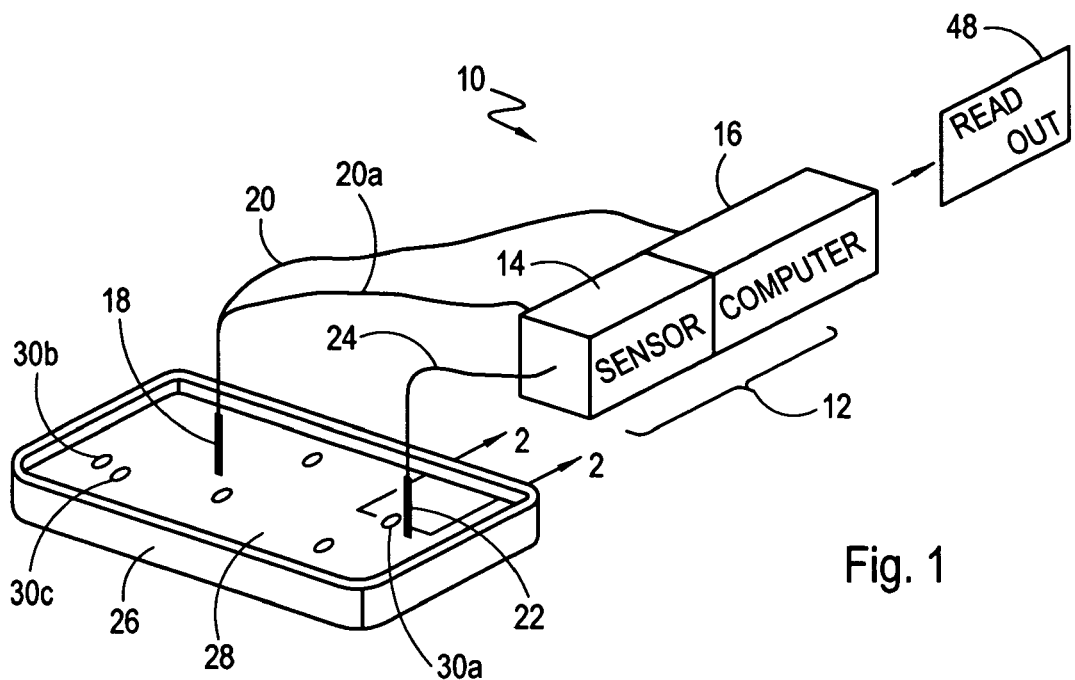
FIG. 1 is a perspective schematic view of the system of the present invention being used in its intended environment.

Referring initially to FIG. 1, a system in accordance with the present invention is shown and generally designated 10. In detail, FIG. 1 shows that the system 10 includes a system electronics unit 12 which has a sensor 14 that may be electronically connected to a computer 16, if desired. Further, the system 10 is shown to include a reference electrode 18 that may be electronically connected to the computer 16 via a line 20, also if desired. Alternatively, the reference electrode 18 may be electronically connected to the sensor 14 via a line 20a. The system 10 also includes a probe 22 that is electronically connected to the sensor 14 via a line 24.

Still referring to FIG. 1 it is seen that an intended operational environment for use of the system 10 includes a tray 26, or sealed enclosure, for holding a nutrient bath 28. As intended for the present invention, the nutrient bath 28 is appropriately selected to provide the proper nutrients and electrolyte conditions for maintaining the particular biological entities to be evaluated. Typically, these biological entities will be cells 30 (of which the cells 30a, 30b and 30c are only exemplary) that are taken from the group of all cells comprising animal cells, plant cells, neurons, bacterial specimens and amoebae. Additionally, the cells 30 can be modified, for example by the insertion of protein pores or genetically modified cells 30 can be used.

Figure 2:
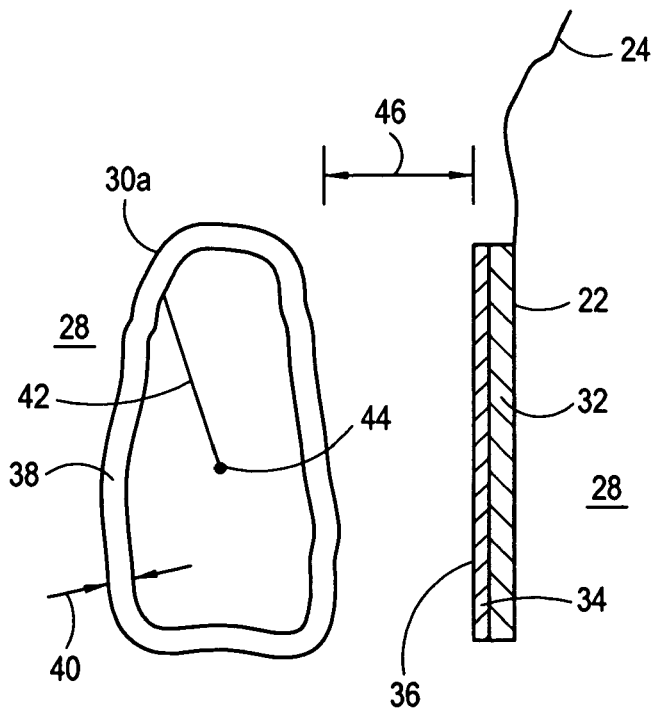
FIG. 2 is a cross sectional view of the probe of the present invention and a cell whose electrical potential is being measured by the probe, as seen along line 2—2 in FIG. 1.

Referring now to FIG. 2, it is seen that the probe 22 includes an electrode 32 that is covered by a dielectric insulator 34 to protect the probe 22 from direct resistive contact with the nutrient bath and cell. The conducting surface 36 of the probe 22 senses the electric potential produced over its volume by the cell 30a. As is well known by the skilled artisan, these signals are indicative of the potential within the cell 30a. Still referring to FIG. 2 the general structure of an exemplary cell 30a is shown. Specifically, the cell 30a is shown to have an outer membrane with a thickness 40 that is about ten nanometers (nm). Also, the cell 30a has an averaged radius 42 that extends from the center 44 of the cell 30 to the membrane 38 and is equal to about ten microns (10 $\mu$m).

Figure 3:
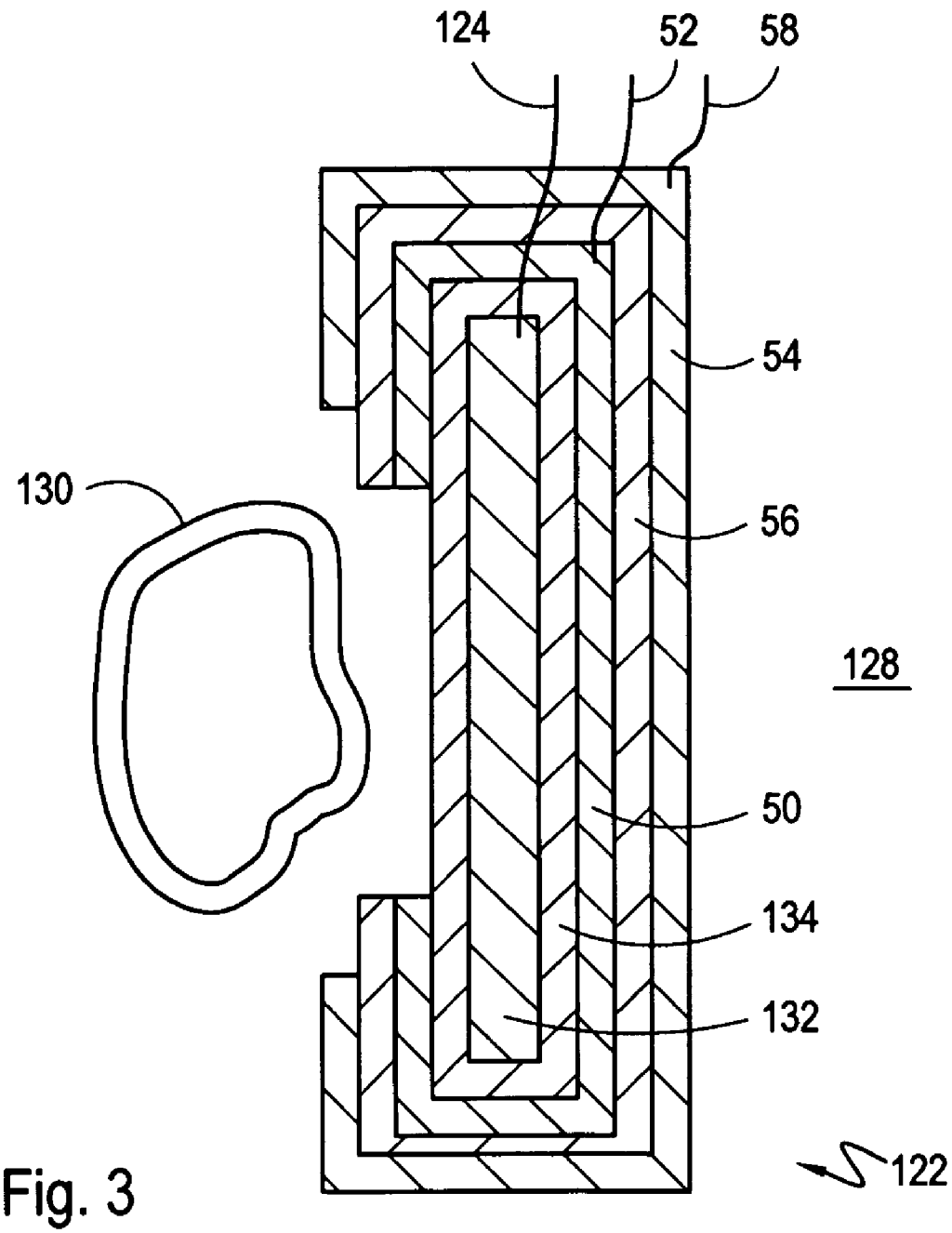
FIG. 3 is a cross sectional view of another embodiment of a probe for the present invention.

Referring now to FIG. 3, another embodiment of a probe (designated probe 122) for use in the present invention is shown. As shown, the probe 122 includes an electrode 132 that is covered by a dielectric insulator 134. For this embodiment of the present invention, a dielectric insulator 134 is provided to prevent electrical contact between the electrode 132 and the nutrient bath 128. A line 124 connects the electrode 132 to the sensor 14 (sensor 14 shown in FIG. 1). As further shown in FIG. 3, the probe 122 includes a guard 50 that partially surrounds the covered electrode 132 and is connected to the sensor 14 (shown in FIG. 1) by line 52. With this cooperation of structure, an opening in the guard 50 allows the cell 130 to approach the covered electrode 132. Typically, the opening will have approximately the same spatial extent as the cell 130, as shown. In accordance with the present invention, the guard 50 can be maintained at substantially the same potential as the electrode 132 to prevent capacitive coupling between the electrode 132 and the nutrient bath 128.

Continuing with FIG. 3, it can be seen that the probe 122 further includes a conducting layer 54 (that is also insulated from the nutrient bath 128). An insulating layer 56 is disposed between the conducting layer 54 and the guard 50 to isolate the conducting layer 54 from the guard 50. As further shown, line 58 is provided to connect the conducting layer 54 to the sensor 14 (shown in FIG. 1). In accordance with the present invention, the potential of the conducting layer 54 can be controlled to minimize the distortion of the electric fields within the nutrient bath 128, minimize coupling between adjacent probes 122 when multiple probes 122 are used, or to maximize the measured signal.

In another embodiment of a probe 122 (not shown), a portion or all of the sensor 14 (shown in FIG. 1) can be attached to the electrode 32, 132 for movement therewith. For this embodiment, batteries for powering the attached portion of the sensor 14 can be coupled with the electrode 32, 132 and the attached portion of the sensor 14 or the batteries can be positioned remotely and connected to the sensor 14 using a cable.

Preferably, the electrode 32, 132, line 24, 124 and other regions of the signal input to the sensor 14 are isolated from the outside world by an impedance of at least 1 G$\Omega$, and more preferably 100 G$\Omega$, at the frequency of interest. Further, the sensor 14 is preferably stable with respect to drift at its input due to the input bias current of its first stage amplifier when connected to the purely capacitive input of the electrode 132. Additionally, it is preferable that the current and voltage noise of the first stage amplifier in the sensor 14 is sufficiently low so that when connected to the purely capacitive impedance of the electrode 32, 132, the cell signal can be measured with adequate fidelity over the required bandwidth.

A suitable circuit for use in the sensor 14 is disclosed in co-pending U.S. patent application Ser. No. 09/783,858 for an invention entitled "Low Noise, Electric Field Sensor," filed on Feb. 13, 2001, which is assigned to Quantum Applied Science and Research Inc. The entire contents of U.S. application Ser. No. 09/783,858 are incorporated by reference herein. Alternatively, a circuit having an impedance of sufficiently high value at the signal of interest to provide a current path to the sensor ground without reducing the signal presented at the amplifier input to an unacceptably low level can be used in the sensor 14.

In operation, the reference electrode 18, and the probe 22 are both immersed or are otherwise positioned into the nutrient bath 28. When a cell (e.g. cell 30a) comes within a distance 46 of the probe 22, the probe 22 picks up a signal from the cell 30a. For purposes of the system 10 of the present invention, the distance 46 will effectively be somewhere within a range from zero to approximately ten microns. Preferably, the distance 46 will be around one micron, or one-half micron. Regardless the extent of the distance 46, the potential that is received by the conducting surface 36 of the probe 22 is applied at the input of the sensor 14. It is noted that in order to optimize the received signal, the conducting surface 36 and the cell 30a should be about the same size. In any event, as the signal from cell 30a is being sent to the sensor 14, a reference potential for the nutrient bath 28 is simultaneously sent from the reference electrode 18 to the computer 16. The electronics unit 12 then compares the signal received from the cell 30a with the reference potential for the nutrient bath 28. The result is a read out 48 that is indicative of the electrical potential of the cell 30a with respect to the bath. It will be appreciated by the skilled artisan that several cells 30 can be measured at the same time. The result in this latter case will be an integrated response. Either way, the read out can be used to evaluate the condition and activity of the cell or cells 30 in a manner well known to those skilled in the pertinent art.

In accordance with the methods of the present invention, the change in a cell's electrical potential that occurs in response to the exposure of the cell to a biological, chemical or pharmacological substance can be measured. Specifically, the electrical potential of the unexposed cell 30 can first be measured as described above. Next, the cell 30 can be exposed to an agent such as a biological, chemical or pharmacological substance. In one implementation, the agent is simply added to the nutrient bath 28. After the addition, the electrical potential of the exposed cell 30 can be continuously monitored to determine whether and when the exposure has altered the cell 30, and the corresponding change in the cell's electrical potential. Once a cell's response to an agent has been measured, this information can be used, for example, to determine the exposure history of another cell (of the same cell type).

By way of example, the strength of a signal from a cell 30, and the general signal to noise ratio (SNR) that is received by the unit 12 can be estimated. Assuming 20% of the charge on cell 30a is opposite the conducting surface 36 of the probe 22, it can be shown that a total charge on the order of $3 \times 10^{-16}$ C will be coupled from the cell 30a into the electronics unit 12. This will give an input voltage to the sensor 14 of around one hundred micro volts (100 $\mu$V). Alternatively, the fraction of voltage from cell 30a that is coupled into the sensor 14 can be approximately given by the expression $C_{electrode}/(C_{electrode-cell}+C_{sensor})$. This expression predicts an input signal of one hundred sixty micro volts (160 $\mu$V). Thus, even for a single small cell 30a, the SNR of over 100 is predicted at frequencies above 10 Hz. For larger cells, the signal will, of course, be increased.

While the particular Circuit and Method to Non-Invasively Detect the Electrical Potential of a Cell or Neuron as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for non-invasively measuring the electrical potential of a cell in a nutrient bath according to a signal radiated by the cell, said system comprising:
    a probe including an electrode covered by an electrically insulating material, a guard partially surrounding said electrode, and a means for maintaining said guard at substantially the same potential as said electrode to minimize capacitive coupling between said electrode and the bath, said probe being positioned within a predetermined distance from the cell to receive the signal therefrom;
    a reference electrode immersed into the bath to determine a reference potential for the nutrient bath;
    a sensor electronically connected to said probe for recording the signal radiated by the cell in the nutrient bath; and
    a sensor means for comparing the reference potential to the signal radiated from the cell to measure the electrical potential of the cell.

2. A system as recited in claim 1 wherein said predetermined distance is in a range between one-half micron (0.5 $\mu$m) and ten microns (10 $\mu$m).

3. A system as recited in claim 1 wherein said probe has a detection surface and the cell and said detection surface have a substantially same spatial extent.

4. A system as recited in claim 1 wherein a cell-probe capacitance is established when said probe is within said predetermined distance, and wherein the cell-probe capacitance is less than approximately one one-hundredth picofarad (0.01 pF).

5. A system as recited in claim 1 wherein the signal radiated by the cell has a frequency greater than about ten Hertz (>10 Hz) and said sensor records the signal with a signal to noise ratio (SNR) greater than one (SNR>1).

6. A system as cited in claim 1 wherein the cell is a biological entity.

7. A system as recited in claim 6 wherein the biological entity is selected from a group consisting of animal cells, plant cells, neurons, bacterial specimens and amoebae.

8. A system as recited in claim 1 wherein said sensor records signals radiated from a plurality of cells.

9. A system as recited in claim 1 wherein said probe further comprises a conducting layer and a means for controlling the potential of said conducting layer to a predetermined potential relative to said reference potential to minimize the distortion of electric fields within the nutrient bath.

10. A system for non-invasively measuring the electrical potential of a cell according to a signal radiated by the cell, said system comprising:
    a means for maintaining the cell for radiation of a signal therefrom;
    a means for positioning a cell within a predetermined distance from a probe including an electrode covered by an electrically insulating material, a guard partially surrounding said electrode and a means for maintaining said guard at substantially the same potential as said electrode to minimize capacitive coupling between the electrode and the means for maintaining the cell and a detecting surface for receipt of the signal from the cell by the detecting surface, said surface being located on the insulating material;
    a means electrically connected to said positioning means for recording the signal radiated by the cell in said maintaining means; and
    a sensor means for using the signal radiated from the cell to measure the electrical potential of the cell.

11. A system as recited in claim 10 further comprising:
    a means for determining a reference potential for the maintaining means; and
    a means for comparing the reference potential to the signal to measure the electrical potential of the cell.

12. A system as recited in claim 10 wherein said maintaining means is a nutrient bath.

13. A system as recited in claim 10 wherein said recording means is a sensor.

14. A system as recited in claim 10 wherein said predetermined distance is in a range between one half micron (0.5 $\mu$m) and ten microns (10 $\mu$m).

15. A system as recited in claim 10 wherein the cells and said conducting surface have a substantially same spatial extent.

16. A system as recited in claim 10 wherein the signal radiated by the cell has a frequency greater than about ten Hertz (>10 Hz) and said recording means records the signal with a signal to noise ratio (SNR) greater than one (SNR>1).

17. A system as recited in claim 10 wherein the cell is a biological entity selected from a group consisting of animal cells, plant cells, neurons, bacterial specimens and amoebae.

18. A method for non-invasively measuring the electrical potential of a cell according to a signal radiated by the cell, said system comprising:
    maintaining the cell in a nutrient bath for radiation of a signal from the cell;

positioning the cell within a predetermined distance from a probe, said probe including an electrode covered with an electrically insulating material, and a guard partially surrounding said electrode, said material having a conducting surface for receipt of the signal from the cell by the conducting surface;

maintaining said guard at substantially the same potential as said electrode to minimize the capacitive coupling between the electrode and the nutrient bath;

determining a reference potential for the nutrient bath;

recording the signal radiated by the cell in the nutrient bath; and comparing the reference potential of the nutrient bath to the signal radiated from the cell to measure the electrical potential of the cell.

19. A method as recited in claim 18 wherein said predetermined distance is in a range between one half ten microns (0.5 µm), and ten microns (10 µm) wherein the signal radiated by the cell has a frequency greater than about ten Hertz (>10 Hz) and is recorded in said recording step with a signal to noise ratio (SNR) greater than one (SNR>1).

20. A method as recited in claim 19 wherein the cell is a biological entity selected from a group consisting of animal cells, plat cells, neurons, bacterial specimens and amoebae.

21. A method as recited in claim 18 further comprising the steps of:

exposing the cell to an agent selected from the group of agents consisting of a biological agent, a chemical agent and a pharmacological agent;

recording the signal radiated by the exposed cell in the nutrient bath; and comparing the reference potential of the nutrient bath to the signal radiated from the exposed cell to measure the electrical potential of the exposed cell.

22. A system for non-invasively measuring the electrical potential of a cell in a nutrient bath according to a signal radiated by the cell, said system comprising:

a probe including a guard partially surrounding an electrode and a means for maintaining said guard at substantially the same potential as said electrode to minimize capacitive coupling between said electrode and the nutrient bath and being positioned within a predetermined distance from the cell to receive the signal therefrom:

a reference electrode immersed into the nutrient bath to determine a reference potential for the nutrient bath;

a sensor electronically connected to said probe for recording the signal radiated by the cell in the nutrient bath; and a sensor means for comparing the reference potential to the signal radiated from the cell to measure the electrical potential of the cell.

23. A system as recited in claim 22 wherein said probe further comprises a conducting layer and a means for controlling the potential of said conducting layer to a predetermined potential relative to said reference potential to minimize the distortion of electric fields within the nutrient bath.

* * * * *